United States Patent [19]

Dencks et al.

[11] Patent Number: 4,989,975
[45] Date of Patent: Feb. 5, 1991

[54] ATOMIC ABSORPTION SPECTROMETER

[76] Inventors: Carl G. Dencks, Prielstrasse 3; Gunther Roedel, Hunter den Garten 13, both of 7776 Owingen/DE; Klaus P. Rogasch, TH-Hofmannweg 3, 7772 Uhldingen - Muhlhofen 1/DE, all of Fed. Rep. of Germany

[21] Appl. No.: 439,404

[22] PCT Filed: Mar. 13, 1989

[86] PCT No.: PCT/EP89/00258
§ 371 Date: Nov. 16, 1989
§ 102(e) Date: Nov. 16, 1989

[87] PCT Pub. No.: WO89/08831
PCT Pub. Date: Sep. 21, 1989

[30] Foreign Application Priority Data

Mar. 18, 1988 [DE] Fed. Rep. of Germany ....... 3809216

[51] Int. Cl.$^5$ .................... G01N 21/31; G01N 21/72; G01N 21/74
[52] U.S. Cl. .................... 356/307; 356/312; 356/315; 356/319
[58] Field of Search ............... 356/311, 315, 312, 319, 356/244, 307

[56] References Cited

U.S. PATENT DOCUMENTS 4,406,541  9/1983  Tomoff et al. .................... 356/312

FOREIGN PATENT DOCUMENTS 1964469  10/1973  Fed. Rep. of Germany .
2950195   6/1981  Fed. Rep. of Germany .
2165106   2/1984  Fed. Rep. of Germany .
3528300   2/1987  Fed. Rep. of Germany .

Primary Examiner—F. L. Evans
Attorney, Agent, or Firm—Thomas P. Murphy; Edwin T. Grimes

[57] ABSTRACT

In an atomic absorption spectrometer with an atomizing device (190) and a line emitting light source (16), an optical system (22,28. . . ) for generating a measuring light beam (18), and a photo-electrical detector (38), which are arranged in a housing (10) which forms a sample cavity (12) accessible from the outside and which is passed through by a measuring light beam (18) and into which different atomizing devices can be optionally inserted, the atomizing device (190) with the specific components (104,124,126) is assembled to form an insert unit (100) in which the atomizing device (190) in the form of a graphite furnace has a well-defined position relatively to the insert unit (100) and which in turn can be inserted into the sample cavity (12) in a well-defined position to provide an entirely functioning atomic absorption spectrometer.

10 Claims, 9 Drawing Sheets

ATOMIC ABSORPTION SPECTROMETER

TECHNICAL FIELD

The invention relates to an atomic absorption spectrometer comprising
(a) an atomizing device for atomizing a sample which is to be analyzed such that the atoms of the element contained in the sample are present in atomic state in an atomization area,
(b) a line emitting light source
(c) an optical system for generating a measuring light beam originating from a line emitting light source and passing through the atomization area,
(d) and a photo-electrical detector to which the measuring light beam is passed by the optical system after passing through the atomization area, wherein
(e) the light source, the optical system and the photo-electrical detector are arranged in a housing which forms a sample cavity accessible from outside, which is passed through by a measuring light beam and which is arranged for different atomizing devices optionally being inserted.

Atomic absorption spectrometers serve for determining the amount or concentration of an element looked for in a sample. For this purpose a measuring light beam from a line emitting light source, a hollow cathode lamp for example, is directed to a photo-electrical detector. An atomizing device is arranged in the path of rays of this measuring light beam. The sample which is to be analyzed is atomized in this atomizing device such that the components of the sample are present in atomic state. The measuring light beam contains the resonant lines of the element looked for. These resonant lines of the measuring light beam are absorbed by the atoms of the element looked for in the cloud of atoms, while ideally the other elements contained in the sample do not influence the measuring light beam. Therefore the measuring light beam is subjected to an attenuation which is a measure of the number of the atoms looked for in the path of the measuring light beam and thus a measure of the concentration or the amount of the looked-for element in the sample, depending on the method of atomization applied. The absorption to which the measuring light beam is subjected is not only caused by the atoms of the element looked for. There is a "background absorption" due to the absorption of the light by molecules for example. This background absorption has to be compensated with particularly highly sensitive measurements.

A flame may serve as atomizing device into which a sample is sprayed in as a solution, for high sensitive measurements the electrothermal atomization is preferably used: The sample is introduced into a furnace which is heated to high temperature by passing electrical current therethrough. Thereby the sample is dried at first, then ashed and at last atomized. Then a "cloud of atoms" is generated in the furnace in which cloud the atom looked for is present in atomic state. The measuring light beam is passed through this furnace.

The "Zeeman effect" is used for background compensation. When a magnetic field is applied to the absorbing atoms in the atomized sample splitting and shifting of the resonant lines of these atoms is effected. Then the resonant lines of the atoms no longer coincide with the spectral lines of the measuring light beam and no atomic abosorption takes place in the borderline case. This permits discrimination between non-atomic background absorption which is also present when the magnetic field is applied, and real atomic absorption which is superposed to the background absorption when the magnetic field is not applied.

The invention relates to an advantagous construction of such an atomic absorption spectrometer.

BACKGROUND ART

From German patent application No. 1,964,469 an atomic absorption spectrometer is known wherein the radiation originates from a single light source designed as a line emitter, the radiation of which passing through the sample is frequency modulated by use of the longitudinal Zeeman effect. In this prior atomic absorption spectrometer a hollow cathode lamp is arranged between the pole pieces of a solenoid. One of the pole pieces has a bore through which the measuring light beam passes. Then the measuring light beam is directed through a flame serving as atomizing device and a monochromator and impinges upon a photo-electrical detector. The solenoid is arranged to be switched on and off, whereby the atomic absorption of the sample atoms compensated with respect to the background absorption can be determined from the difference of the signals with the solenoid switched off and switched on.

In this prior art atomic absorption spectrometer the emission lines of the line emitting light source are periodically shifted by the Zeeman effect and thus the emitted light frequency is modulated and not the absorption lines of the sample. This may cause problems when a hollow cathode lamp is used as light source because the discharge of the hollow cathode lamp is influenced by the magnetic field, as already mentioned in German Patent Application No. 1,964,469.

From German patent application No. 2,165,106 it is known to apply the magnetic field of a solenoid arranged to be switched on and off to the atomizing device, i.e. to the sample which is to be atomized, instead to the light source. Therein the atomizing device is a flame. The magnetic field is applied perpendicular to the direction of propagation of the measuring light beam. A splitting of the absorption lines due to the "transverse" Zeeman effect is effected, which again effects a relative shift of the emission lines of the measuring light beam and the absorption lines of the sample. Again it can be discriminated between atomic absorption by the atoms of the element looked for and non-specific background absorption by switching the magnetic field on and off.

From German patent application No. 2,165,106 an atomic absorption spectrometer is known in which a sample cavity is formed by a housing which sample cavity is passed through by a measuring light beam. An atomizing device is arranged in the sample cavity. A measuring vessel in which hydrides are decomposed which were formed from a sample by chemical reactions, a burner or a furnace for electrothermal atomization (graphite tube vessel) can be optionally provided as atomizing device.

With respect to the prior art German patent application No. 29 50 105 describes a construction in which depending on the kind of atomization the suitable atomizing device is individually built into the sample cavity and is adjusted in the sample cavity. After building in and after adjustment the connections for the supply of current, inert gas and cooling liquid or for fuel gas and oxidant agent have to be installed.

Compared thereto German patent application No. 29 50 105 describes an atomic absorption spectrometer in which at least two of the above mentioned atomizing devices, hydride measuring vessel, burner or furnace are composed to a componentry which is fixedly installed in the sample cavity. The measuring light beam can be optionally passed through a respective atomization device being in operation.

German patent application No. 29 50 105 relates only to the installation of the atomizing device in a narrow sense that means the burner or the furnace. Each mode of operation however requires additional apparatus. A burner requires control devices for controlling or regulating the fuel gas or oxydant agent supplies. A power unit which supplies the high and adjustable currents required belongs to a furnace for the electrothermal atomization. These additional apparatus are generally designed as separate components which are arranged beside the atomic absorption spectrometer and generally are quite clumsy. The atomic absorption spectrometer according to German patent application No. 29,50,105 allows no compensation of the background absorption in that the atomic absorption of the atoms of the sample is "eliminated" by the Zeeman effect by means of a magnetic field applied.

In the atomic absorption spectrometer of German patent application No. 29 50 105 discussed before all atomizing devices which can be optionally used are permanently installed in the apparatus. Also the signal processing has to be provided for the different modes of atomization. Thereby the atomic absorption spectrometer becomes clumsy and expensive.

From German patent application No. 35 28 300 an atomic absorption spectrometer with a burner is known in which the burner is adjustably arranged on a carriage. The carriage is movable between a first and a second position by a servomotor. In a first position the cloud of atoms is generated by the burner in the area of the measuring light beam extending stationary. In the second position the burner with its flame is arranged outside the measuring light beam extending stationary, such that a measurement is made which is not influenced by the atomized sample. Here the compensation of the drift of the zero line is the subject matter.

A further atomic absorption spectrometer is known in which compensation of the background absorption is permitted by periodically generating a strong magnetic field at the location of the sample in a furnace for electrothermal atomization, whereby the absorption lines of the sample are shifted relative to the lines of the measuring light beam by the Zeeman effect. In this prior atomic absorption spectrometer an atomic absorption spectrometer arranged for operating without "Zeeman effect" is used as basic instrument. A "Zeeman auxiliary apparatus" is attached to this basic apparatus, this auxiliary apparatus comprising a furnace in an additional sample cavity and a solenoid for generating the Zeeman effect.

DISCLOSURE OF THE INVENTION

It is the object of the invention to construct an atomic abosorption spectrometer such that optionally spectrometers for different atomizing devices can be constructed, in manufacturing, from uniform component units.

A further object of the invention is to enable the user to retrofit an atomic absorption spectrometer in a simple way in order to use it with other atomizing devices.

Finally the user shall be enabled to choose in a simple way between different atomizing devices.

According to the invention these objects are achieved in that (f) the atomizing device with the specific components of the atomizing device are assembled to an insert unit in which the atomizing device has a well-defined position relative to the insert unit which, in turn, is arranged to be inserted into the sample cavity in a well-defined position to provide an entirely functioning atomic absorption spectrometer.

According to the invention the atomic absorption spectrometer consists of a basic instrument which comprises the light source, the optical system and the detector. The atomizing device and the specific components of the atomizing device are assembled in an insert unit which is arranged to be inserted into the basic instrument in a well-defined position. In case of a furnace for the electrothermal atomization the specific components of the atomizing device include a power unit and, when the background absorption is measured by Zeeman effect, additionally a solenoid, a power unit and the control for this solenoid and a signal processing circuit for the compensation of the background absorption, if required. When the atomizing device is a burner the specific components include the control or regulating device for fuel gas and oxydant agent and the fixing device for the flame and a flame guard for example. In each case a compact construction is achieved because the specific components (auxiliary apparatus) required for each atomizing device are integrated with the actual atomizing device to an insert unit. The insert unit is arranged in the sample cavity of the basic instrument in an exactly defined position. The atomizing device in turn, that means burner or furnace, are exactly adjusted relative to the insert unit. Therefore the change from one type of atomizing device to another type can be achieved without any problems and without expensive adjusting. There is the advantage for manufacturing that uniform component units are produced which can be assembled to produce a desired type of atomic absorption spectrometer, a flame instrument, for example. At any time the user can retrofit an apparatus by an appropriate insert unit for another kind of atomizing device. The atomic absorption spectrometer in its original version does not require more devices than have been required for the function of the original version.

In contrast to the conventional atomic absorption spectrometer discussed above in which the atomizing devices alone are arranged to be mounted in the sample cavity, in the atomic absorption spectrometer according to the invention the atomizing devices with the associated, specific components are integrated in a insert unit and are adjustable relatively thereto.

In contrast to the arrangement of German patent application No. 29 50 105 there are not several atomizing devices which are provided permanently in the atomic absorption spectrometer.

In contrast to the prior "Zeeman" atomic absorption spectrometer discussed above no additional apparatus with a separate sample cavity is required. On the contrary also an atomizing device operating with compensation of the background absorption by the Zeeman effect can be inserted into the provided sample cavity.

In contrast to all prior atomic absorption spectrometers discussed hereinbefore in the atomic absorption spectrometer of the present invention the auxiliary apparatus are integrated in the insert unit.

Modifications of the invention are subject matter of the sub-claims.

An embodiment of the invention will now be described in further detail with reference to the accompanying drawings.

PREFERRED EMBODIMENT OF THE INVENTION

Figure 1:
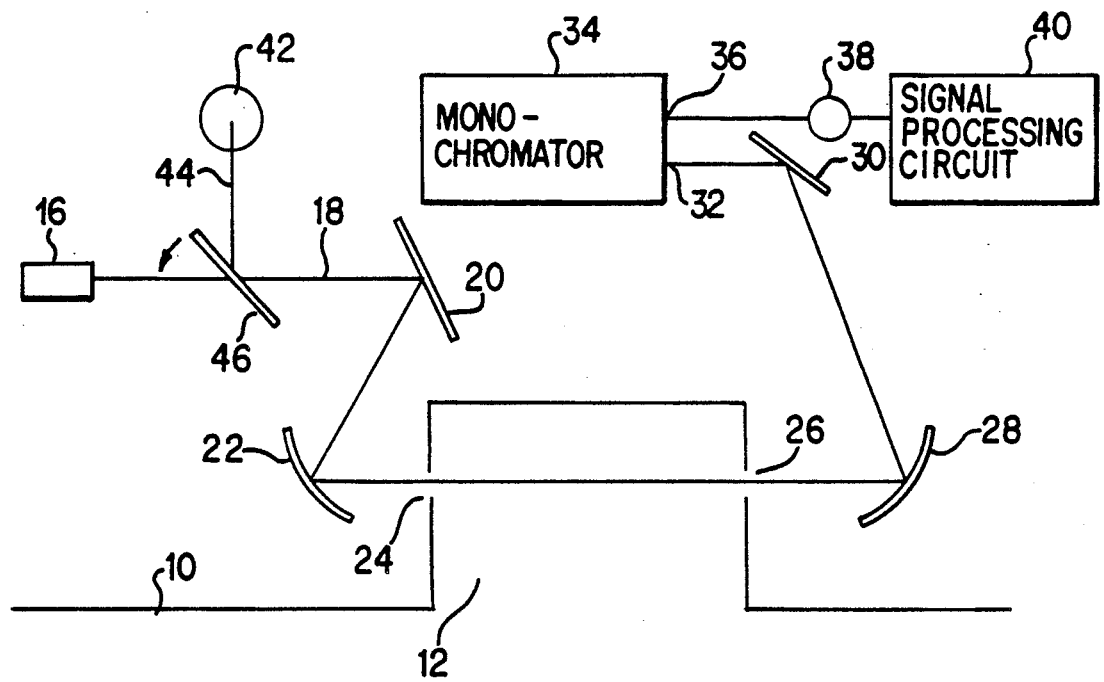
FIG. 1 shows a schematical illustration of the construction of the basic apparatus of an atomic absorption spectrometer.

The atomic absorption spectrometer has a housing 10 in which the lamps, the optical system and the photosensitive detector are arranged. The housing defines a sample cavity 12.

The atomic absorption spectrometer has a hollow cathode lamp as first light source 16. The light source 16 emits a line spectrum which corresponds to the resonant lines of a certain element looked for. A measuring light beam 18 originates from the light source 16. The measuring light beam 18 is deviated by a plane mirror 20 and collected in the center of the sample cavity by a concave mirror 22 through an opening 24 of the housing 10. Then the measuring light beam passes through an opening 26 of the housing 10 aligned with the opening 24 and impinges upon a second concave mirror 28. The second concave mirror 28 focusses the measuring light beam 18 through a plane mirror 30 on the inlet slit 32 of a monochromator 34. A photo-electrical detector 38 is arranged behind an outlet slit 36 of the monochromator 34. The signal of the photo-electrical detector 38 is supplied to a signal processing circuit 40.

A second light source 42 emitting a continuum is arranged in the housing. This second light source is a deuterium lamp. The second light source 42 emits a light beam 44. This light beam 44 from the second light source 42 can be deflected into the path of rays of the measuring light beam 18 through a beam splitter 46 which optionally is movable into the path of rays of the measuring light beam 18. The first and the second light source 16 and 42, respectively, are arranged to be switched on alternately in a quick sequence such that a measuring light beam 18 with a line spectrum from the first light source (hollow cathode lamp) 16 or a measuring light beam with a continuum from the second light source (deuterium lamp) 42 passes alternately through the cloud of atoms generated in the furnace body.

Figure 2:
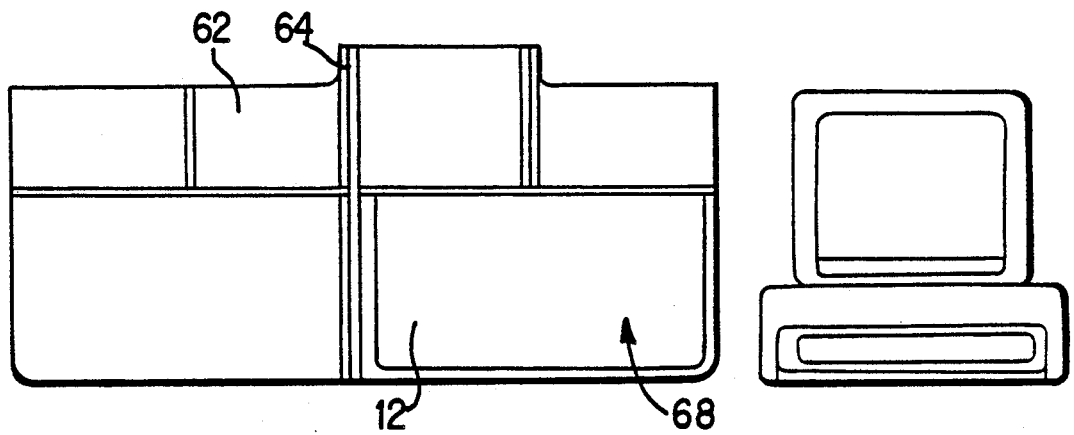
FIG. 2 shows a front view of the basic apparatus.
Figure 3:
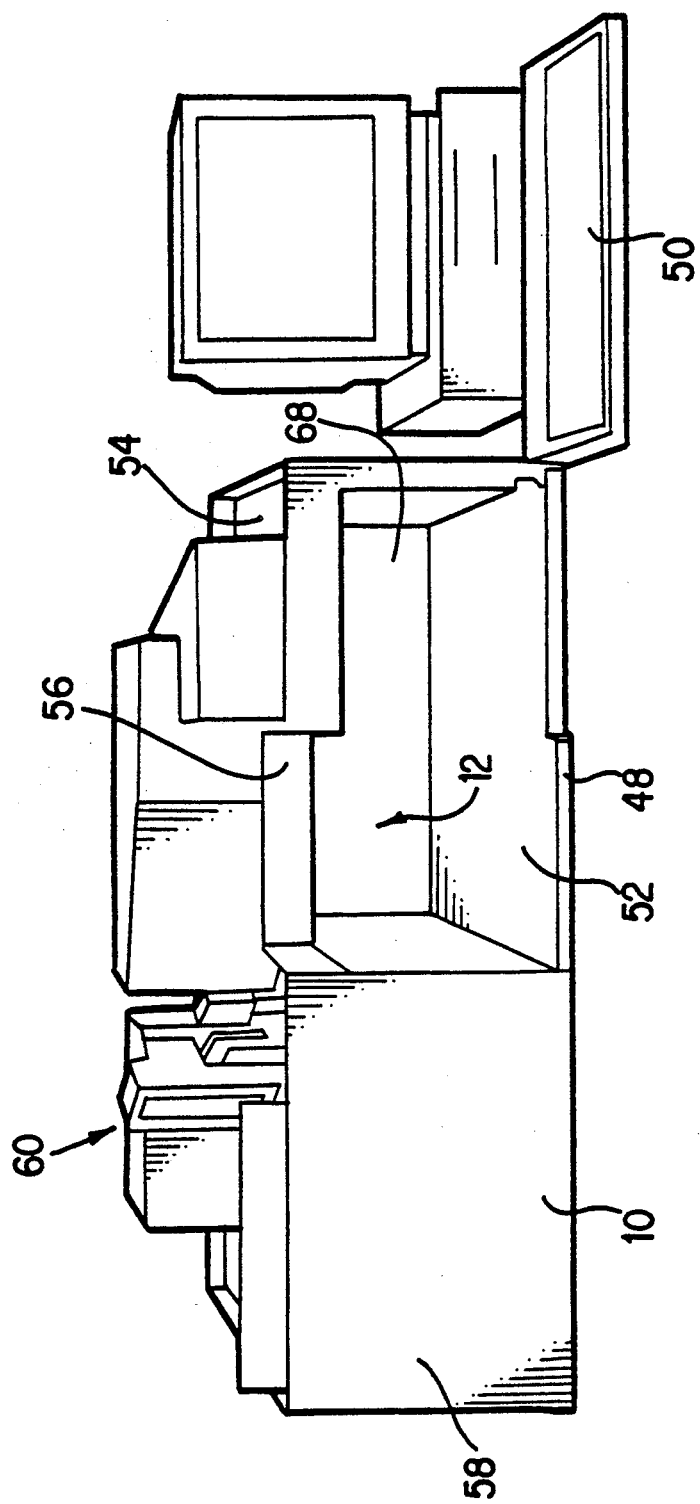
FIG. 3 shows a perspective illustration of the basic apparatus the cover of the optical portion being removed.

FIG. 2 and FIG. 3 show the spatial construction of the basic apparatus 48 which is connected with a computer 50. The housing 10 of the basic apparatus 48 forms the sample space 12. The housing 10 forms a base 52 and a carrier plate 54 spaced above this base 52 on which carrier plate the light source, the optical system and the photo-electrical detector are arranged. The carrier plate has a rectangular cutout 56 at its front side. A closed compartment 58 is formed in the housing 10 on one side of this cutout which compartment contains the "basic electronics" which is common for all atomizing devices used together with the basic apparatus. Numeral 60 designates all components mounted on the carrier plate 54. The components are covered by a hood 62. This hood 62 forms an edge 64 projecting upwardly arround the cutout 56 the apertures 24 and 26 for the passage to the optical system being provided. The sample cavity 12 open to the front side is formed in this way below the cutout 56 and above the base 52. The sample cavity forms a rectangular recess of the housing 10. Optical members of the optical system are arranged on both sides of this recess. The sample cavity 12 is limited to the left in FIG. 3 by a partion wall 66 below the carrier plate 54 which partion wall closes the compartment 58. A cavity 68 communicates with the sample cavity at the rear and at the right in FIG. 3.

Insert units can be inserted into the sample cavity 12 and the cavity 68 in a defined position. Each of these insert units contains an atomizing device and the specific components of this atomizing device, again in a well-defined position, as will be explained hereinbelow. The respective atomizing device is aligned correctly with the measuring light beam, after the insert unit has ben inserted into the sample cavity 12 and the cavity 68. With the insert unit inserted the atomic absorption spectrometer is entirely functioning for the operation with the respective atomizing device.

Figure 4:
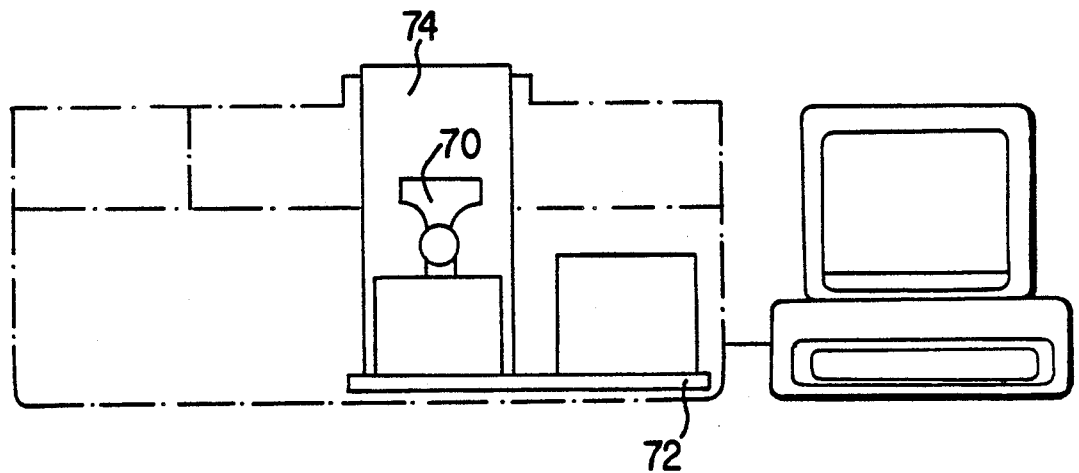
FIG. 4 shows a front view of an atomic absorption spectrometer in which the atomizing device is formed by a burner.
Figure 5:
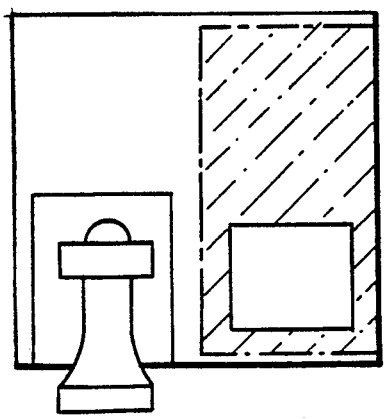
FIG. 5 shows a plan view on a insert unit with a burner and a "gas box".
Figure 6:
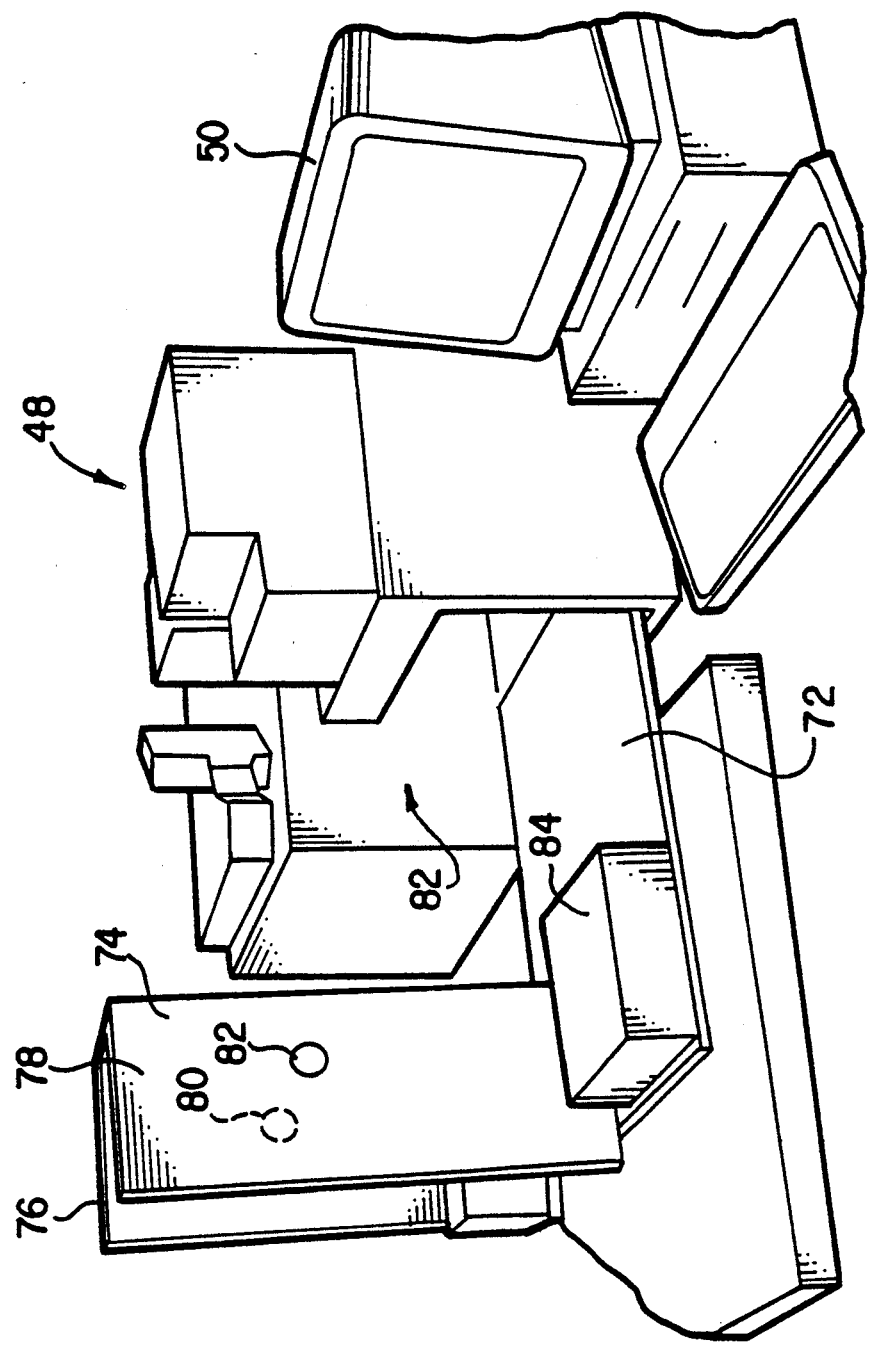
FIG. 6 shows a perspective illustration of the basic apparatus with the insert unit containing the burner and the gas box, the insert unit being partially pulled out.

FIG. 4 and FIG. 6 show an atomic absorption spectrometer in which a burner 70 is provided as atomizing device. The burner is arranged on an insert plate 72. The burner 70 is surrounded by a protective housing 74 which is open to the front and to the top. The protective housing 47 has a cuboid shape and is open to the front on a longitudinal surface and open to the top on an end face. Aligned apertures 80 and 82, respectively, are provided in the longitudinal surfaces 76 and 78 which are adjacent to the open longitudinal surface at the front. The measuring light beam 18 passes through these apertures when the insert unit is inserted into the sample cavity 12. Further more, a controlling and regulating device 84 for the supply of fuel gas and oxydant agent to the burner 70 is provided on the insert plate 72. Besides space for further specific element, particularly the associated electronics for the operation with a burner is provided on the insert plane 72. These elements are not illustrated in FIGS. 4, 5 and 6 for clarity.

Figure 7:
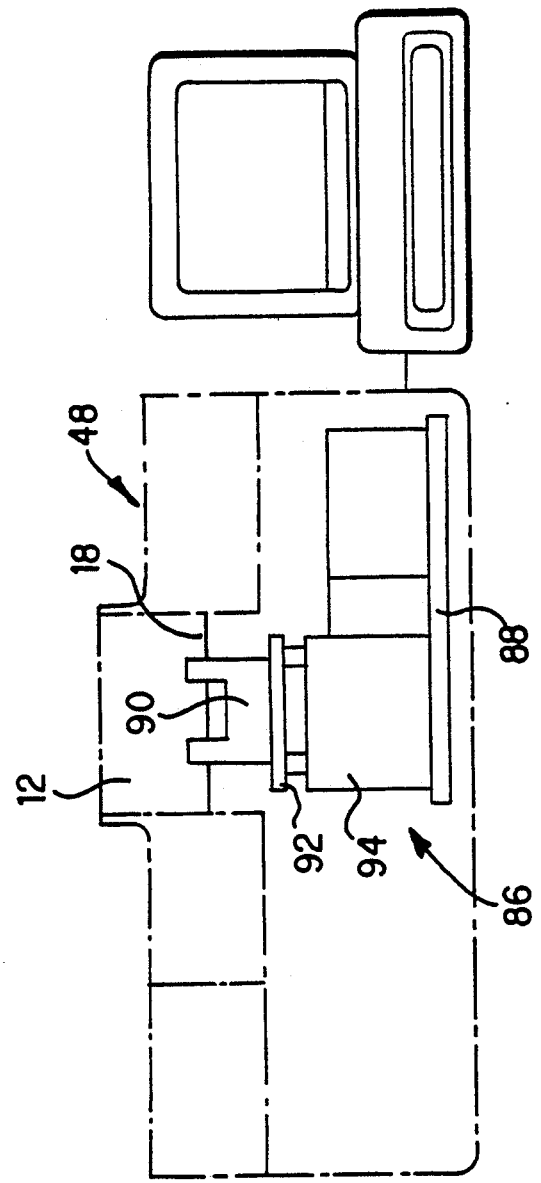
FIG. 7 shows a front view of an atomic absorption spectrometer in which the atomizing device is formed by a furnace for the electrothermal atomization of the sample.

FIG. 7 shows the basic apparatus 48 with an insert unit 86 with a furnace for the electrothermal atomization of the sample (graphite tube vessel) as atomizing device.

The furnace 90 is arranged on an insert unit 88 on an adjustable intermediate platform 92. A power unit 94 with a transformer for the current supply to the furnace is arranged below the intermediate platform 92. As illustrated in FIG. 7 the furnace projects into the sample cavity 12 to the top between the optical members (concave mirror 22 and 28 in FIG. 1) and into the path of rays of the measuring light beam 18. Beside the furnace 90 and the power unit 92 the other specific components required for the operation of the furnace, particularly the electronics and the pneumatic control are arranged on the insert plate. These components are provided in an intermediate housing 96.

Figure 9:
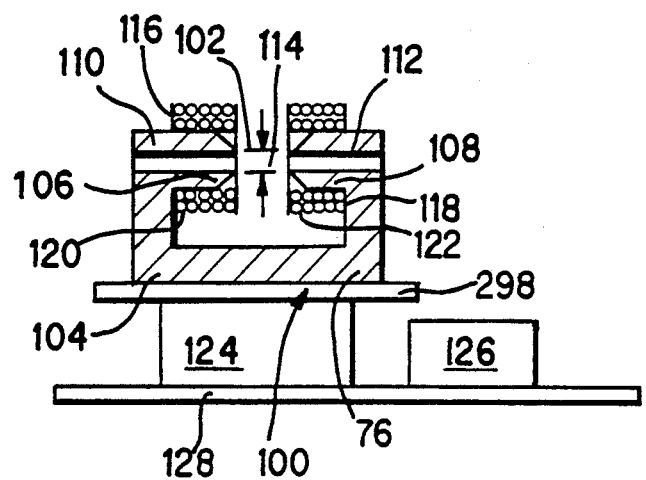
FIG. 9 shows a schematical illustration of an insert unit with a furnace for the electrothermal atomization of the sample and a solenoid by means of which a shift of the absorption lines of the atoms of the sample can be effected making use of the Zeeman effect.

FIG. 9 shows schematically an insert unit 100 in which a furnace for the electrothermal atomization of the sample is provided as atomizing device and a magnetic field can be generated at the location of the sample by a solenoid in order to measure the background absorption, this magnetic field causing a shift of the absorption lines relative to the lines of the measuring light beam by the Zeeman effect.

The atomizing device 100 comprises a furnace for electrothermal atomization, only the actual furnace body 102 of the furnace device being illustrated in FIG. 9, and a solenoid 104 which is arranged to be switched on and off in order to generate a magnetic field at the location of the sample. The solenoid 104 has two aligned pole pieces 106 and 108 between which the furnace body 102 is arranged. Aligned bores 110 and 112 are provided in the pole pieces 106 and 108. The bores 110 and 112 are aligned with a longitudinal bore 114 of the furnace body 102. The measuring light beam 18 passes through the bores 110 and 112 and through the longitudinal bore 114 of the furnace body 102. Coil holders 116 and 118 are arranged on the pole pieces 110 and 102, respectively. Coils 120 and 122 of the solenoid 104 are wound on these coil holders 116 and 118, respectively. Numeral 124 designates a power unit which controls the current through the furnace body 102. As indicated the current is supplied transversely to the direction of the measuring light beam 18 and flows through the tubular furnace body 102 in circumferential direction. The solenoid 104 is controlled by a magnet control 126 such that the magnetic field alternately is switched on and off. At the location of the sample the magnetic field of the solenoid 104 is directed within the furnace body in the direction of propagation of the measuring light beam 18. Therefore the longitudinal Zeeman effect is generated at the sample atoms when the magnetic field is switched on. That means that the absorption lines of the sample atoms are split into two lines, each, which are shifted relative to the undisturbed original absorption line. There is no atomic absorption in the sample with the wave length of the original absorption line. Therefore also the atoms of the elements looked for do not absorb the measuring light beam 18 because this measuring light beam contains only the non-shifted resonant lines which are characteristic of the element. Therefore only the background absorption is measured when the magnetic field is switched on. The component of real atomic absorption corrected with respect to the background absorption can be determined from the measurements with the magnetic field switched on and off. For this purpose the cycle of switching the solenoid 104 on and off is supplied to the signal evaluation circuit 40 (FIG. 1). The elements of the signal processing circuit particularly required for the "Zeeman measurement" are mounted on an insert plate 128 together with the solenoid 104, the furnace 114 the power unit 124 and solenoid control 126. The atomic absorption spectrometer is entirely functioning as "Zeeman apparatus" with the insert unit.

In this mode of operation with the beam splitter 46 moved into the path of rays the solenoid 104 is switched off. Then the background absorption can be determined in that the absorption of the very narrow spectral line of the first light source 16 and the absorption of a band of continuum radiation, which is relatively wide compared to the spectral line, determined by the monochromator 34, is measured. The change between the first light source 16 and the second light source 42 is made at a frequency of more than 500 cycles per second, namely 1000 cycles per second. The way of operating with a second light source emitting a continuum as reference light source permits detection of relatively quick changes of the background absorption which could not be detected when using the Zeeman effect by means of the solenoid 104. The solenoid 104 is relatively sluggish such that the frequency of the change between atomic absorption measurement and background measurement is limited. By application of the longitudinal Zeeman effect no polarizer is required in the path of rays. Therefore the atomic absorption spectrometer can operate with a second light source 42 emitting a continuum without causing double attenuation of the light by the polarizer and additionally by the beam splitter 46, the solenoid being switched off.

Figure 8:
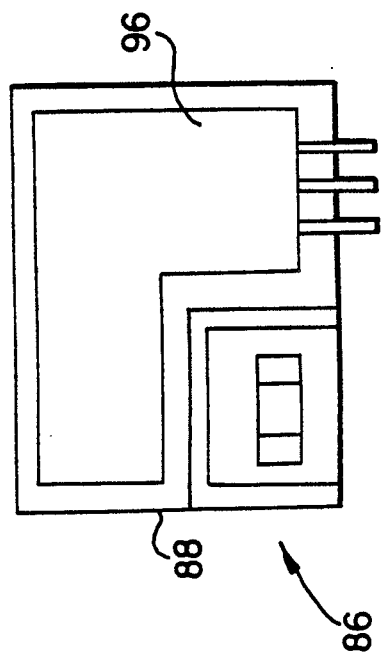
FIG. 8 shows a plan view of the insert unit with furnace and with the associated electronical and pneumatic componentries.

Therefore the "Zeeman" insert unit permits optionally also to operation with the solenoid 104 being switched off and a deuterium lamp being used for determining the background absorption. In any case the deuterium lamp is required for the measurement with a simple furnace according to FIG. 7 and FIG. 8.

Figure 11:
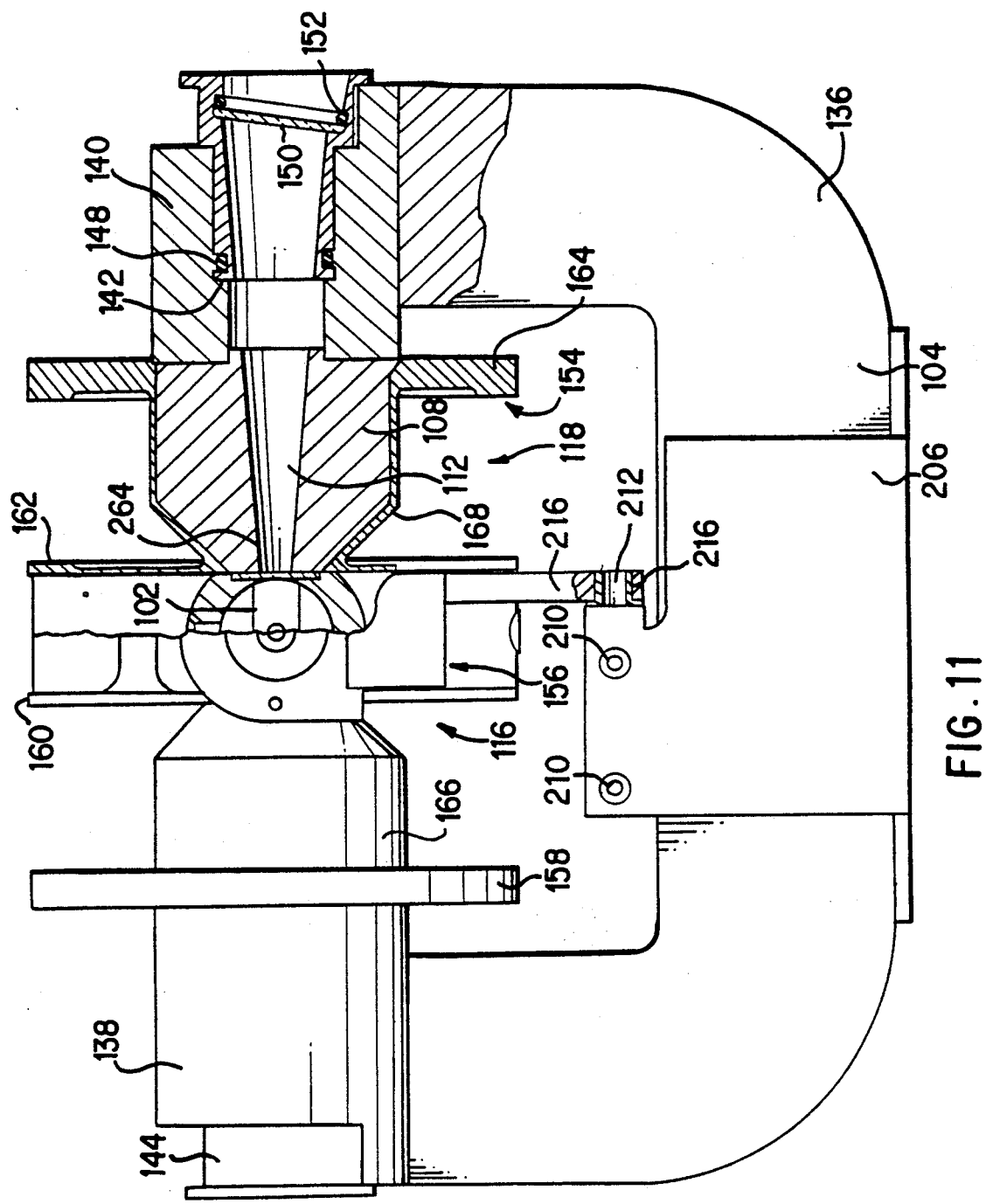
FIG. 11 shows a particularly advantageous embodiment of the "Zeeman" arrangement which promotes a particularly compact construction of the solenoid and thereby the design as insert unit.
Figure 12:
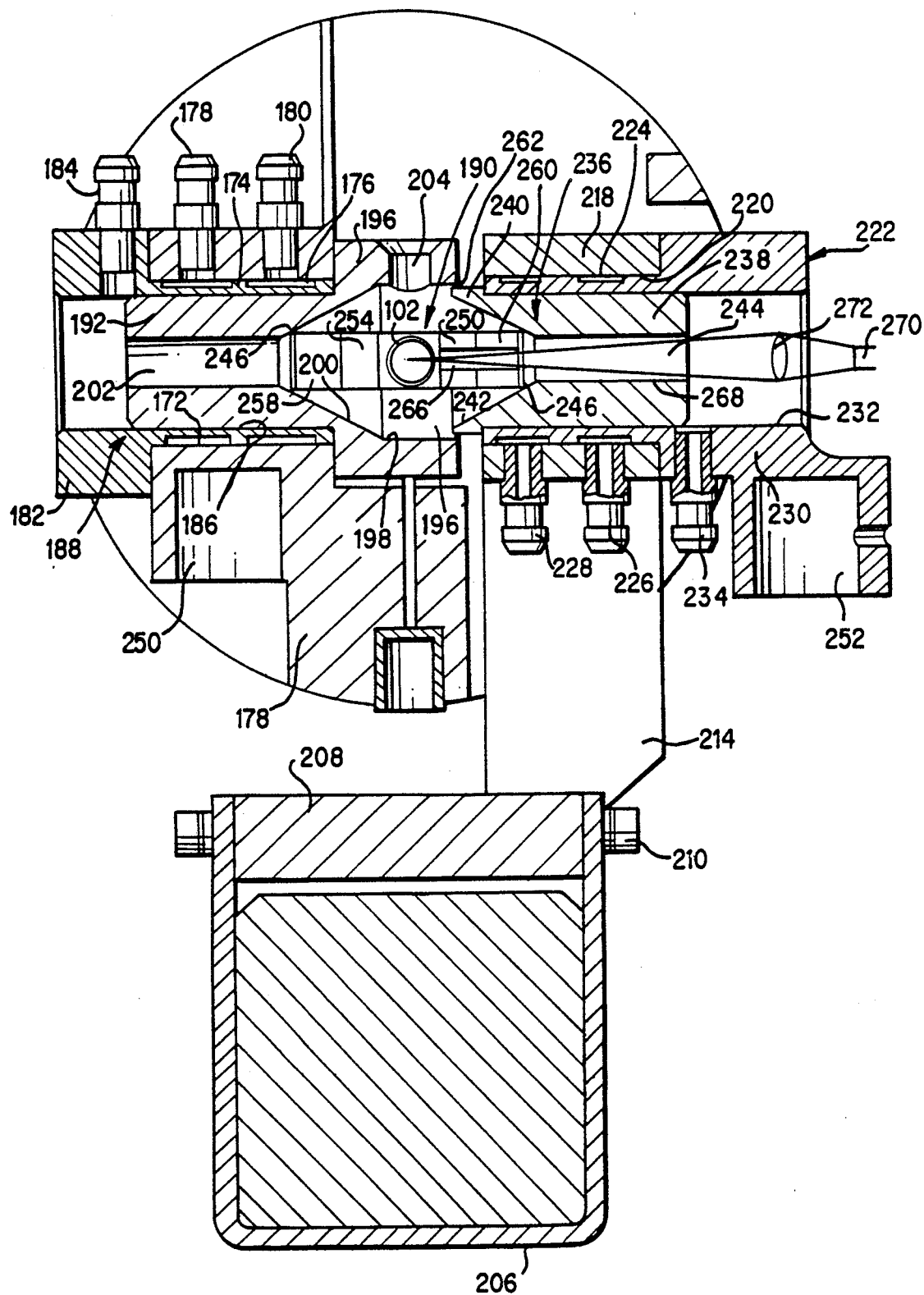
FIG. 12 shows a sectional view taken along the lines XII—XII of FIG. 11.

The construction of the atomizing device with the solenoid 104 and the furnace is illustrated in detail in FIG. 11 and FIG. 12.

The solenoid 104 has a u-shaped magnetic return path 136 made of laminated iron and aligned pole pieces 106,108. The pole pieces 106 and 108 are cylindrical and are frustro conically tapered at the ends facing each other. The pole pieces 106 and 108 are arranged on the aligned end pieces 138 and 140, respectively, which are provided on the legs of the u-shaped magnetical return path 136 and project inwardly from there. The aligned apertures 110 and 112, respectively, extend through the pole pieces 106 and 108 and the end pieces 138 and 140. The apertures 110 and 112, respectively, are provided by conical inner surfaces in order to ensure focussing the measuring light beam 18 in the center of the furnace body 102. In the area of the ends pieces 138 and 140 the apertures 110 and 112, respectively, form shoulders 142. Window holders 144 and 146, respectively, are inserted into the apertures 110 and 112 and are sealed by O-rings 148. Windows 150 are located in the window holders 144 and 146 which are arranged oblique in the window holders 144 and 146, respectively, in order to avoid reflections, and which are held by sealing rings 152.

An integral element 154 made of a non-magnetic material as aluminum is provided on the pole pieces 106 and 108. This element 154 forms the coil holder 116 and 118 on which the field coils 120 and 122, respectively, are wound, and on the other hand forms a contact carrier 156 which carries one of the contacts between which the furnace is held. The field coils 120 and 122 are not illustrated in FIG. 11 and FIG. 12 for clarity.

The coil holders 116 and 118 are formed by spool-shaped elements with two flanges 158 and 160 or 162 and 164, respectively, and hub portions 166 and 168, respectively. The hub portions 166 and 168 match the shape of the pole pieces 106 and 108, respectively. A block 170 having a bore 172 is arranged between the flanges 160 and 162 facing each other of the two coil hoders 116 and 118. An insert 174 is provided in the bore 172 and has meander-shaped grooves 176 on its outer surface, these grooves together with the inner surface of the bore 172 forming a cooling passage. This cooling passage communicates with an inlet 178 and an outlet 180 for the cooling liquid. The insert has a head portion 182 whereon an inert gas inlet 184 is provided. A central axial bore 186 extends throughout the insert 174 which is closed at its left end in FIG. 12. A contact 188 is provided in this axial bore 186 by which contact a furnace 190 is held on one side for the electrothermal atomization, and through which contact also the current supply for the furnace 190 is accomplished.

The contact 188 has a shaft 192 which is located in the axial bore 186, and a head 194. The head 194 has a recess 196 in its end face. At first this recess 196 is cylindrical in a section 198 adjacent to the end face and then tapers conically in a section 200. A central axial bore 202 extends in the shaft 192 and ends on the bottom of the recess 196. A radial inlet port 204 is formed in the cylindrical section 198 in the head 194 on top in FIG. 12 through which port a sample can be introduced into the furnace 190.

The magnetic return path 136 of the solenoid 104 is surrounded by a sheet metal element 206 having a u-shaped cross-section in which a bearing element 208 is held by a bolt 210. A pivotable arm 214 is pivotably mounted on a pin 212 of the bearing element through a bearing bushing 216. A movable block 218 is provided at the pivotable arm 214. Similar to the block 170 the block 218 has a bore 220. An insert 222 similar to the insert 174 is arranged in the bore 220. The insert 222 has meander-shaped grooves 224 on its outer surface which grooves together with the inner surface of the bore 220 form a cooling passage. This cooling passage communicates at its ends with an inlet port 226 and an outlet port 228 for the cooling liquid. The insert 222 has a head 230. A central axial bore 232 extends through the insert 222 and the head 230. On the right side of FIG. 12 the axial bore 232 is closed by a window. An inert gas port 234 opens into the axial bore 232. A contact 236 is arranged in the axial bore 232. The contact 236 has a cylindrical shaft 238 and a flat head 240. A conical recess 242 is formed in the end face of the head 240. The recess 242 corresponds approximately to the recess section 120. A central axial bore 244 similar to the bore 202, extends through the shaft 238 of the contact 236.

In operational position of the pivotable arm 214, as illustrated in FIG. 12, the furnace 190 is held between the contacts 188 and 236 with conical contact surfaces 246 and 188. Then the contacts 188 and 236 are aligned. The current is supplied to the furnace 190 through the blocks 170 and 218, the inserts 174 and 202 and the contacts 188 and 236. For this purpose the block 170 and the insert 222 are provided with plug-type connectors 250 and 252, respectively, for the high-current cables.

The furnace 190 contacts the actual furnace body 102 which can be recognized best in FIG. 11. Diametrically opposite contact ribs 254 and 196 which can be seen in FIG. 11 extend along the furnace body 102. Substantially cylindrical contact pieces 258 and 260 are adjacent to the contact ribs 254 and 256, said contact pieces are held between the contacts 188 and 236 by the conical contact surfaces 246 and 248. The axes of the contact pieces 258 and 260 are aligned with the axes of the contacts 188 and 236 in the paper plane of FIG. 11 and extend perpendicular to the axis of the furnace body 102 which is aligned with the measuring light beam 18. An inlet port is provided in the furnace body 102 perpendicular to these two axes, that means on the top of FIG. 11 and FIG. 12, this inlet port being aligned with the inlet port 204 and permitting sample to be introduced therethrough into the furnace 190.

The contacts 188 and 236 form a cavity with their recesses 196 and 228, this cavity containing the furnace 190. The contacts 188 and 236 are separated from each other only by a relatively narrow separating gap 262. The pivotable arm 214 can be deflected clockwise in FIG. 12 by a pneumatic tilting device (not illustrated). This is indicated in FIG. 12 by an arrow. Thereby the block 218 with the insert 222 and the contact 236 is deflected and the furnace 190 is accessible. In this way an exchange of the furnace 190 can be accomplished. An inert gas is supplied through the inert gas ports 184 and 234. This inert gas flows through the bores 186 and 232, respectively, and the axial bores 202 and 244, respectively, to the contact pieces 258 and 260, respectively, of the furnace 190. Then the inert gas is distributed in the furnace 190 by passages which still have to be described. The contacts 188 and 236, respectively, and the furnace 190 are made of graphite. The inert gas prevents the furnace 190 from getting into contact with air oxygen, when it is heated, and thus from burning.

A shielding disc 264 with a central aperture for the measuring light beam is arranged between the contact 188 and the end face of the pole piece 108 as can be seen in FIG. 11. The shielding disc 264 is made of pyrolytic plastic with a high heat conductivity in the plane of the shielding disc 264 and a low heat conductivity perpendicular to this plane. In this way the pole piece 108 is protected from high temperatures of the furnace 190 and the contact 188.

The axial bores 232 and 244 in the insert 222 and the contact 236 and the inert gas passage 266 in the contact piece 260 and the contact ledge 256 serve simultanously for accommodating a pyrometer path of rays 268 in which a part of the wall of the furnace element 102 is observed by a radiation detector 270 by means of an imaging system 272. The signal of the radiation detector 270 provides a measure of the temperature of the furnace element 102 and allows control of the furnace temperature.

The construction of the solenoid 104 and the furnace 190 described permits arrangement of the solenoid with its pole surfaces quite close to the furnace such that a small air gap is achieved despite the longitudinal magnetic field. Arranging the field coils on the pole pieces reduces the stray field. The form of the pole pieces causes a higher density of the field lines in the area of the furnace such that a high magnetic field intensity results there. These measures are effective together in order to achieve the magnetic field intensity which is required for the splitting of the spectral lines by the Zeeman effect with relatively low electrical power and small dimensions of the components. This promotes assembling the atomizing device and the specific components to a insert unit.

Figure 13:
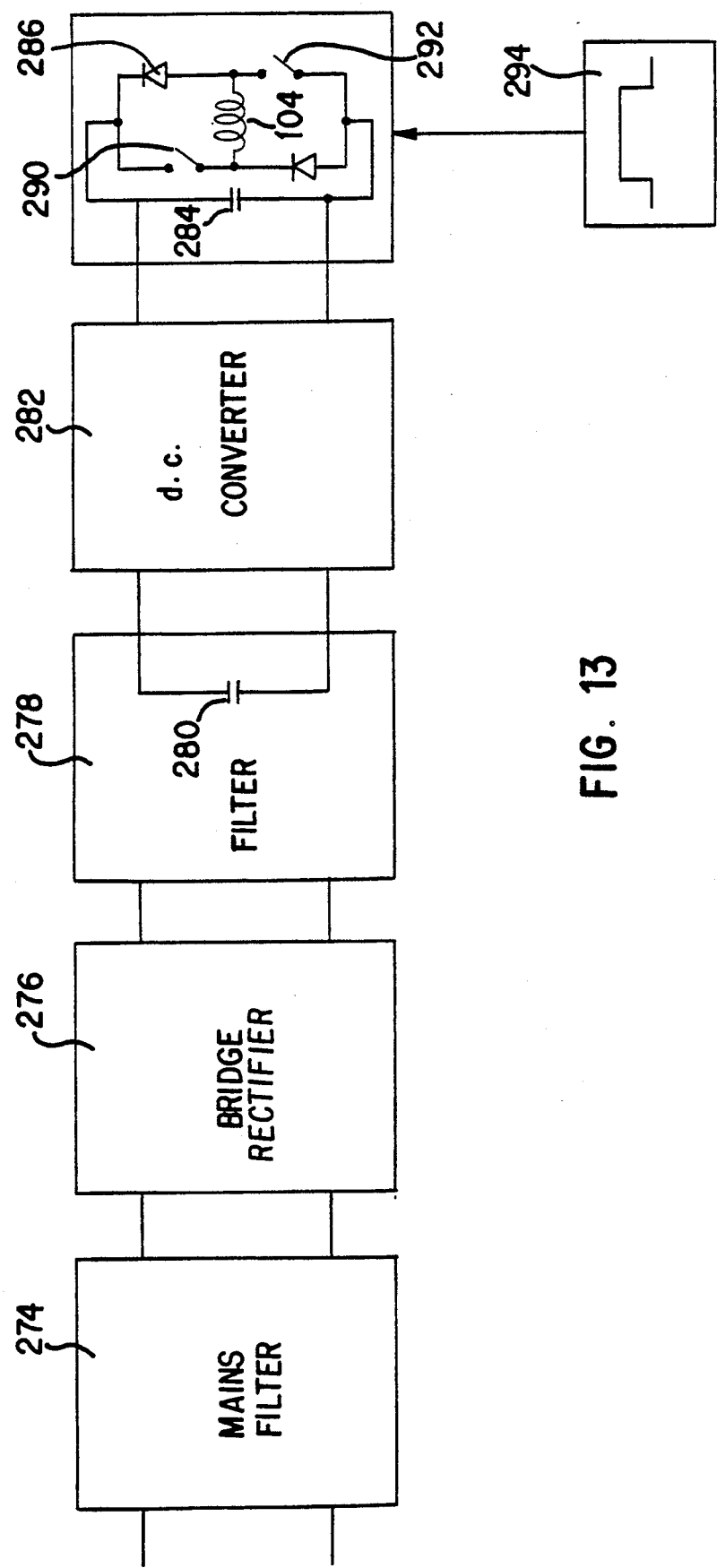
FIG. 13 shows a block diagram of the control of the current by the solenoid in the insert unit of FIG. 9 and FIG. 10.

FIG. 13 shows schematically the control of the current by the solenoid 104. The mains voltage is applied through a mains filter 274 to a bridge rectifier 276. The rectified mains voltage is smoothed by a filter 278 and charges a capacitor 280 serving as energy accumulator. The voltage of the capacitor forms the d.c. input voltage of a d.c. converter 282. The d.c. converter 282 comprises an inverse rectifier which chops the d.c. input voltage at a frequency sufficiently higher than the mains frequency. The alternating voltage obtained in this way is stepped down by a transformer. The alternating current obtained is rectified and charges a capacitor 284 serving also as energy accumulator. The higher frequency permits smaller design of the transformer. The d.c. voltage obtained is applied through diodes 286,288 and controlled switches 290,292 to the capacitor 284. The switch 292 is controlled by a pulse generator 294 which controls the switching on and switching off of the solenoid 104. During on-time the switch 290 controls the current to maintain a predetermiend value.

In this arrangement favorable measuring times are achieved. The energy stored in the in the magnetic field is passed back to the capacitor through the diodes 286,288, after both switches 290,292 have been opened: The induction current of the solenoid charges the capacitor. In this way the energy consumption of the solenoid is kept relatively low. Thereby and by the stepping-up conversion in the d.c. converter 282 the components are smaller than in prior art instruments of comparable type. This in turn facilitates also accomodating all components on the insert plate 128.

The power unit for the solenoid is subject matter of the patent application "Device for Generating a Magnetic Field in an Atomic Absorption Spectrometer" 07/445,606 filed simultaneously.

Figure 10:
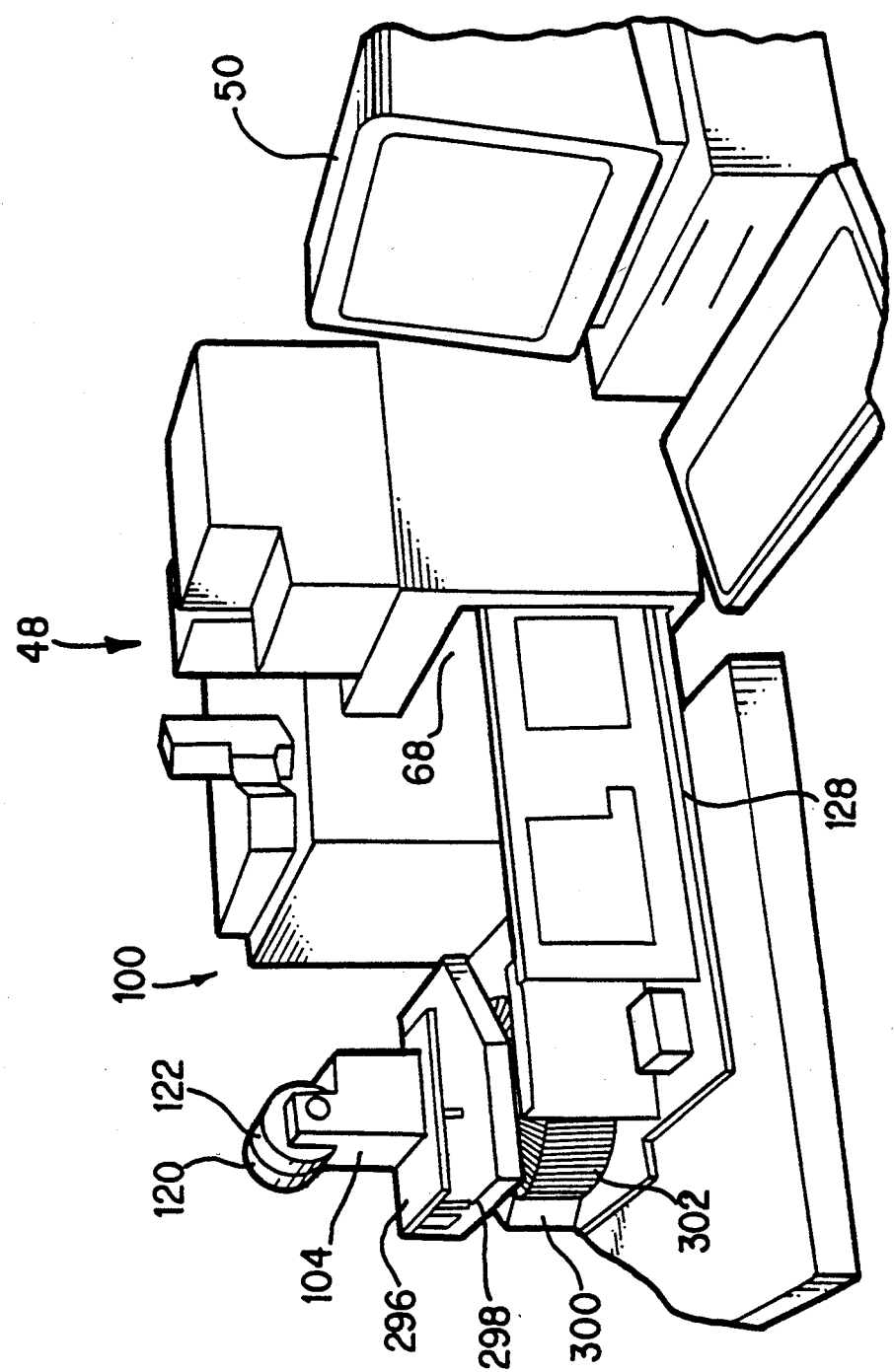
FIG. 10 shows a perspective illustration of the basic apparatus and the "Zeeman" insert unit, the insert unit being partially pulled out.

FIG. 10 is a perspective illustration similar to FIG. 6 and shows the basic apparatus 48 and the insert unit 100. The solenoid 104 and the furnace (not illustrated in FIG. 10) are arranged on an adjustable platform 296. The adjustable platform 296 in turn is arranged on a fixed platform 298 which is supported on supports 300 on the insert plate 128. The transformer 302 of the power unit 124 is arranged on the insert plate 128 below the platform 298.

Beside the furnace and the solenoid 104 the electrical and electronical components for the supply and control of the furnace and the solenoid 104 and the signal processing circuit specific for this kind of measurement are arranged on the insert plate 128.

When the insert unit 100 is inserted into the basic apparatus 48 the solenoid 104 and the furnace are placed in the sample cavity 12 such that the measuring light beam 18 passes through the bores 110,112 and the furnace body 114. The other components are accomodated by the cavity 68.

We claim:

1. Atomic absorption spectrometer comprising
    (a) an atomizing device for atomizing a sample which is to be analyzed such that the atoms of the element contained in the sample are present in atomic state in an atomization area,
    (b) a line emitting light source
    (c) an optical system for generating a measuring light beam originating from a line emitting light source and passing through the atomization area,
    (d) and a photo-electrical detector to which the measuring light beam is passed by the optical system after passing through the atomization area, wherein
    (e) the light source, the optical system and the photo-electrical detector (38) are arranged in a housing which forms a sample cavity accessible from outside, which is passed through by a measuring light beam and which is arranged for different atomizing devices optionally being inserted,
characterized in that
    (f) atomizing devices are assembled to distinct insert units in which the atomizing devices have well-defined positions relative to the insert unit which in turn are arranged to be singly inserted into the sample cavity in a well-defined position to provide an entirely functioning atomic absorption spectrometer.

2. Atomic absorption spectrometer as set forth in claim 1, characterized in that each insert unit contains circuits for controlling and/or signal processing which are specific for the atomizing device.

3. Atomic absorption spectrometer as set forth in claim 2, characterized in that
    (a) the sample cavity of the housing comprises a recess in the housing which recess extends to the top beyond the measuring light beam and which is passed through by the measuring light beam,
    (b) optical elements of the optical system are arranged in the area of the measuring light beam on both sides of the recess, and
    (c) a cavity for accommodating the components of the insert unit specific for the respective atomizing device is formed adjacent to this recess.

4. Atomic absorption spectrometer as set forth in claim 3, characterized in that the atomizing device contains a burner in order to atomize the sample in a flame which burner in combination with a device for controlling or regulating the supply of fuel gas and oxydent agent to the burner (gas box) forms an insert unit.

5. Atomizing device as set forth in claim 4, characterized in that the insert unit for the burner has a protective housing which is open on a longitudinal surface and on an end surface (at the front and on the top), which protective housing surrounds the burner and has apertures for the passage of the measuring light beam in the opposite side walls above the burner, adjacent to the open longitudinal surface.

6. Atomic absorption spectrometer as set forth in claim 5, characterized in that the gas box is arranged on an insert plate projecting laterally relative to the protective housing and is arranged to be inserted with the insert plate into the cavity of the housing.

7. Atomic absorption spectrometer as set forth in claim 3, characterized in that the atomizing device has a furnace for electrothermal atomization, and the power unit for this furnace is part of the insert unit.

8. Atomic absorption spectrometer as set forth in claim 7, characterized in that the atomizing device comprises a solenoid which is arranged to generate a strong magnetic field at the location of the furnace which solenoid effects a shift of the absorption lines of the sample atoms by the Zeeman effect for the purpose of measuring and compensating background absorption, the solenoid being part of the insert unit.

9. Atomic absorption spectrometer as set forth in claim 8, characterized in that the insert unit contains a power unit for the supply and control of the solenoid.

10. Atomic absorption spectrometer as set forth in claim 9, characterized in that
   (a) a second light source is provided which emits a continuum,
   (b) a beam splitter is optionally movable into the path of rays of the measuring light beam and is arranged such that the measuring light beam originating from the second light source is reflected into the path of rays of the measuring light beam, and
   (c) the line emitting light source and the second light source are arranged to be switched on alternately.

* * * * *